United States Patent [19]
Hake

[11] Patent Number: 4,893,613
[45] Date of Patent: Jan. 16, 1990

[54] ENDOSCOPE CONSTRUCTION WITH MEANS FOR CONTROLLING RIGIDITY AND CURVATURE OF FLEXIBLE ENDOSCOPE TUBE

[76] Inventor: Lawrence W. Hake, R.R. #2, P.O. Box 108, Grand Island, Nebr. 68803

[21] Appl. No.: 260,522

[22] Filed: Oct. 21, 1988

Related U.S. Application Data

[63] Continuation of Ser. No. 125,534, Nov. 25, 1987.

[51] Int. Cl.$^4$ .............................................. A61B 1/00
[52] U.S. Cl. ...................................................... 128/4
[58] Field of Search .......................... 128/4, 6; 358/98

[56] References Cited

U.S. PATENT DOCUMENTS

| | | | |
|---|---|---|---|
| 2,844,126 | 7/1958 | Gaylord | 92/90 |
| 4,349,014 | 9/1982 | Takamatsu | 128/6 X |
| 4,620,769 | 11/1986 | Tsuno | 128/6 |
| 4,794,912 | 1/1989 | Lia | 128/4 |

Primary Examiner—William H. Grieb
Attorney, Agent, or Firm—Allegretti & Witcoff, Ltd.

[57] ABSTRACT

An improved flexible endoscope of the type which includes a hollow elongate flexible tube having a distal end which is inserted into a body cavity and a proximal end which is external the body. A sensor system extends through the flexible tube from the proximal end to the distal end. The sensor system is capable of transmitting diagnostic information from the distal end to a sensor system at the proximal end. Means for controlling the flexure of each tube comprises at least one longitudinal expandible conduit positioned radially with respect to the center line axis of the segment. In a preferred embodiment a plurality of inflatable and expandible conduits are provided and pressure means is also provided to inflate the conduits to control rigidity or to expand the conduits longitudinally and sequentially in order to vary the curvature of the tube.

6 Claims, 3 Drawing Sheets

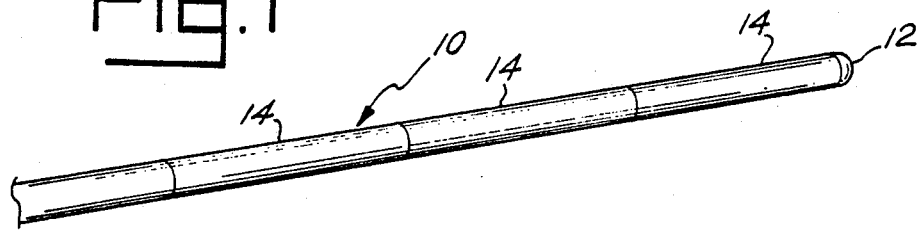
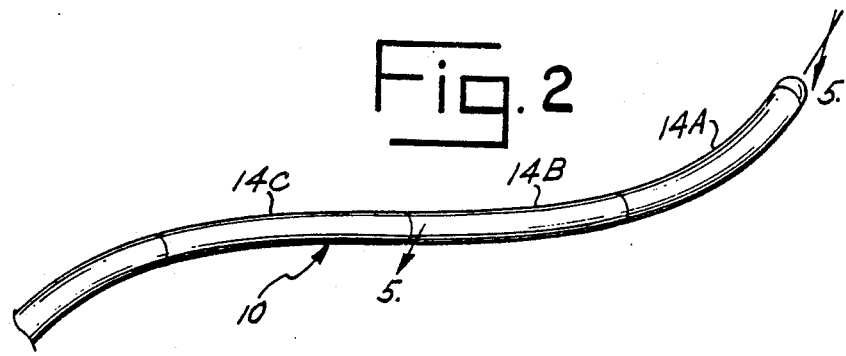
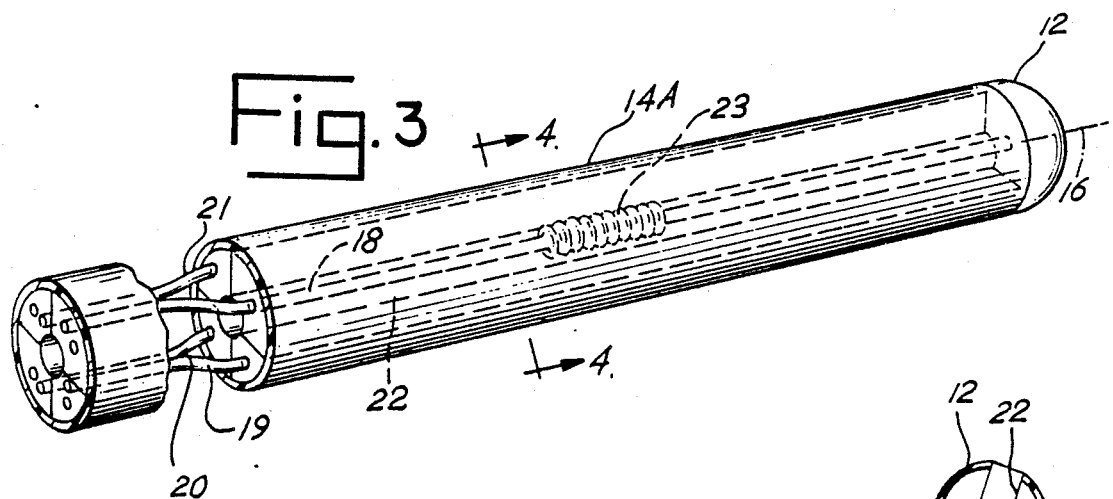
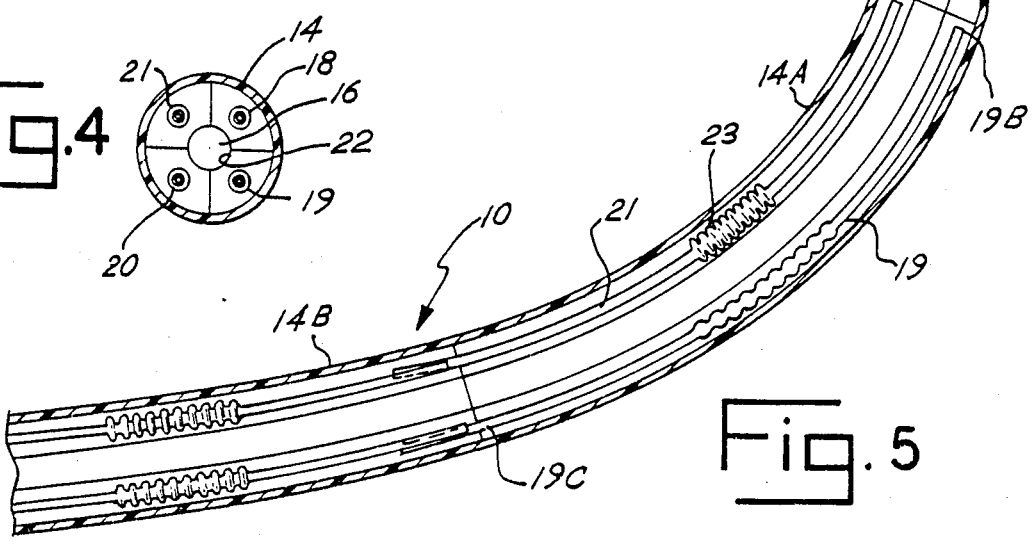

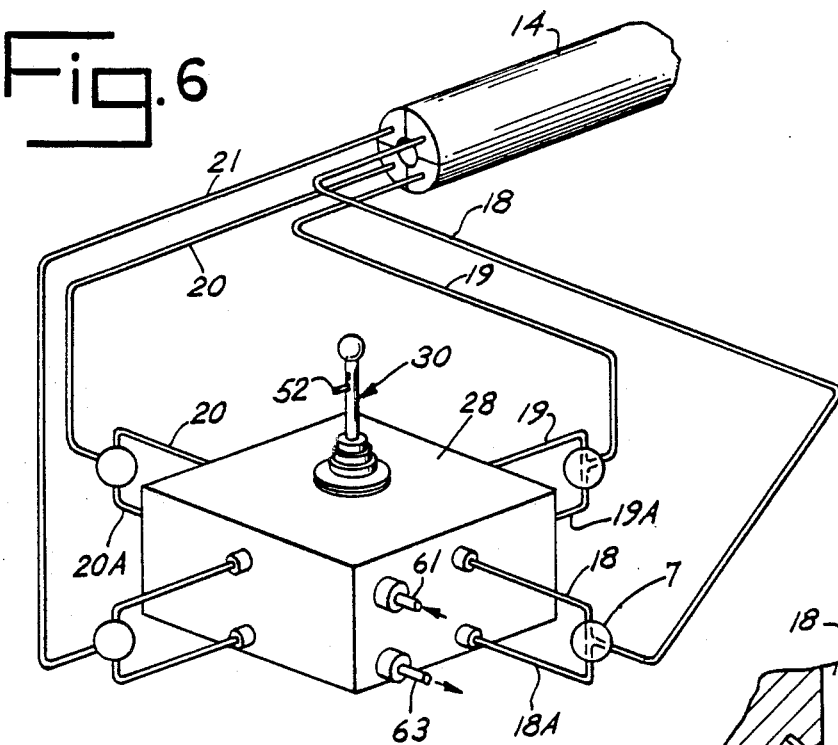
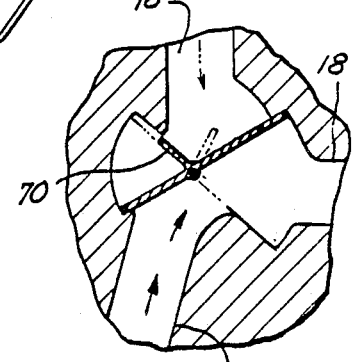
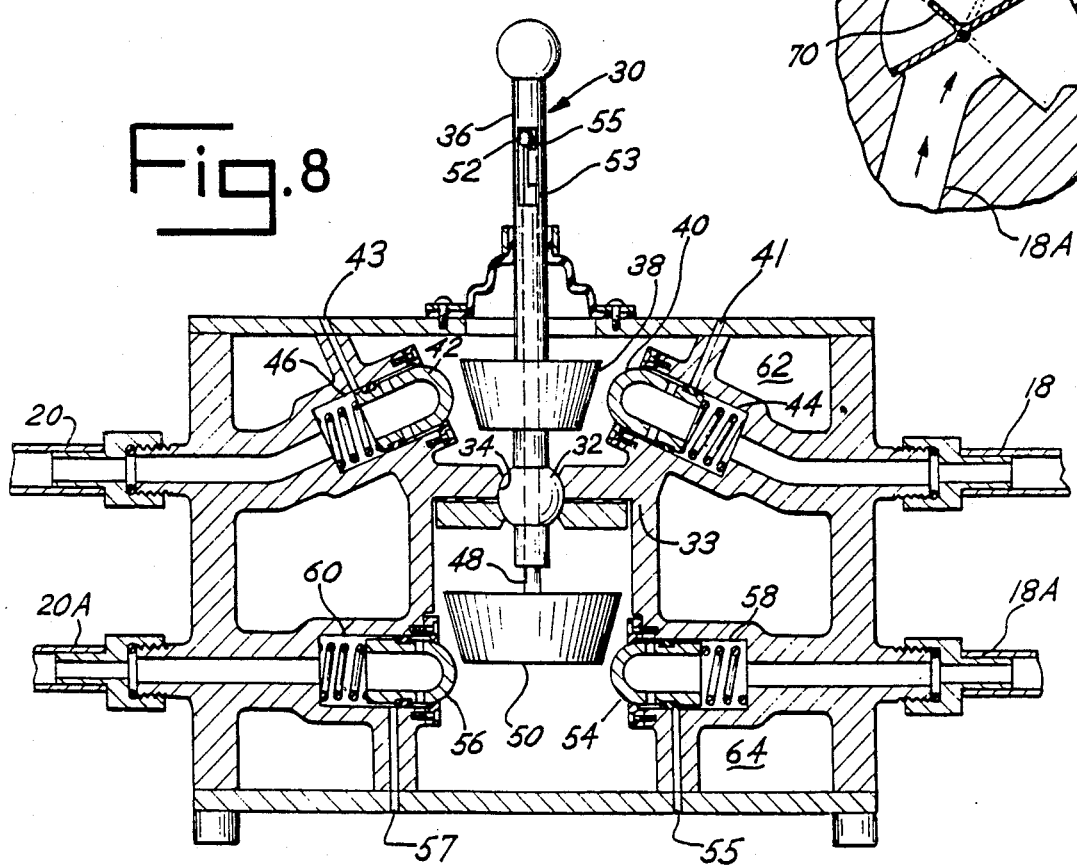

ENDOSCOPE CONSTRUCTION WITH MEANS FOR CONTROLLING RIGIDITY AND CURVATURE OF FLEXIBLE ENDOSCOPE TUBE

This is a continuation of application Ser. No. 125,534, filed 11/25/87.

BACKGROUND OF THE INVENTION

The present invention relates to an improved endoscope construction and more particularly to an endoscope construction including means for controlling the flexure of an endoscope tube especially the rigidity and curvature of the endoscope tube.

The use of an endoscope for diagnostic investigation or other medical intrusion of various body cavities has become an important procedure for physicians. Endoscope devices are known under various medical instrument names; including, flexible cystoscope, flexible neproscope, flexible gastroscope, flexible bronchoscope, flexible choledochoscope, sigmoidoscope, arthroscope, laparoscope and flexible utererscope. Most of the identified endoscopes have a flexible probe or tube which is designed to pass into a curved body passage. The tube typically incorporates a diagnostic or surgical instrument for observation or operation within the body through the tube from outside the body.

In recent years many patents have issued for various types of endoscopes. These patents disclose, for example, use of optical lens or, in recent years, fiber optics to provide for visual diagnosis. Boebel in U.S. Pat. No. 4,503,843 is typical and discloses a device which utilizes a telescope. Seike in U.S. Pat. No. 4,607,619 discloses an endoscope device utilizing a fiber optic or light guide technique. More recently, Arakawa in U.S. Pat. No. 4,651,202 discloses a video endoscope system wherein the diagnostic information is transmitted from the distal end of an endoscope tube via fiber optic fibers to a proximal end where it is transmitted to a cathode ray tube or television.

Endoscopes are also used for performing surgical procedures. A series of patents teach this use of an endoscope including the following:

| U.S. Pat. No. | Inventor | Title | Issue Date |
|---|---|---|---|
| 4,137,920 | Bonnet | Endoscopes | 2/6/79 |
| 4,607,620 | Storz | Medical Gripping Instrument | 8/26/86 |
| 4,625,713 | Hiraoka | Instrument Incorporated in a Resectoscope | 12/2/86 |
| 4,641,634 | Storz | One-Hand Hysteroscope | 2/10/87 |
| 4,653,476 | Bonnet | Instrument Insert for a Uretero-Renoscope | 3/31/87 |

There are additional patents relating to the construction and use of the endoscope instruments including the following:

| U.S. Pat. No. | Inventor | Title | Issue Date |
|---|---|---|---|
| 4,569,333 | Bel, et al | Optical Instrument Including a Focusing Eyepiece and an Endoscope | 2/11/86 |
| 4,576,435 | Nishioka | Endoscope Including a Reflector Related by an Inequality for Uniform Light Distribution | 3/18/86 3/18/86 |
| 4,587,972 | Morantte, Jr. | Device for Diagnostic and Therapeutic | 5/13/867 |

| U.S. Pat. No. | Inventor | Title | Issue Date |
|---|---|---|---|
| 4,633,855 | Baba | Intravascular Intervention Endoscope Apparatus | 1/6/87 |

Generally it is desirable that the endoscope have a flexible tube in order to permit the instrument to follow the circuitous canals and paths defined by body cavities and canals. Many of the prior art references listed above disclose flexible endoscopes.

However, there has remained a need to provide an improved mechanism for controlling the flexure of an endoscope tube in order to more efficiently guide the endoscope through a body cavity. As part of flexure control, there has developed a need to accurately and precisely control the stiffness or rigidity of an endoscope tube. Control of rigidity of the tube is especially critical to facilitate insertion of the tube into a curved body tube or cavity. If the tube is too rigid, insertion may damage the body. If it is too flexible, the tube cannot be properly inserted into the body. As a further part of flexure control, precise control of curvature of the endoscope is desired. These considerations inspired the development of the present invention.

SUMMARY OF THE INVENTION

In a principal aspect, the present invention comprises an improved flexible endoscope of the type which includes a hollow, elongate, flexible tube having a distal end which is inserted into a body cavity and a proximal end which is utilized as a viewing or control end. A sensor system typically extends through the flexible tube from the distal end to the proximal end. The sensor system is capable of transmitting diagnostic information from the distal end to a sensor or observation system at the proximal end.

The invention relates particularly to the means for controlling the flexure (i.e. rigidity and curvature) of the tube. The means for controlling flexure comprises at least one hollow, longitudinal, flexible and optionally expandible conduit incorporated within the endoscope tube and extending longitudinally through the tube. The conduit is preferably positioned radially with respect to the center line axis of a segment of the flexible tube. In a preferred embodiment, there are a plurality of such conduits. Pressure means is also provided to pressurize the conduits and thereby control the rigidity of the associated tube segment. Pressure means also is effective to elastically expand one or more of the conduits longitudinally and sequentially in order to vary the curvature of the tube.

Thus, it is an object of the invention to provide an improved flexible endoscope construction.

Yet a further object of the invention is to provide a flexible endoscope construction which is comprised of a tube having a series of flexible segments, each segment being independently controllable to vary the rigidity and curvature.

A further object of the invention is to provide an endoscope which is flexible and wherein the flexure is controllable by means of fluid pressurizable and elastically expandable conduits parallel to the longitudinal axis of the endoscope and spaced from the centerline axis thereof.

Yet a further object of the present invention is to provide a construction for controlling the rigidity or curvature of segments of an endoscope which system may be incorporated in or with instruments and sensors associated with prior art endoscopes.

Yet a further object of the present invention is to provide a mechanism for controlling the rigidity or curvature of an endoscope which is economical and which is not overly cumbersome or burdensome and therefore may be incorporated efficiently with or as part of existing endoscopes.

A further object of the invention is to provide a construction for independently controlling the rigidity and curvature of at least a segment of a flexible endoscope tube.

Another object of the invention is to provide a construction for controlling the rigidity or curvature or both of a series of segments forming at least part of a flexible endoscope tube.

These and other objects, advantages and features of the invention will be set forth in the detailed description which follows.

BRIEF DESCRIPTION OF THE DRAWING

In the detailed description which follows, reference will be made to the drawing comprised of the following figures:

FIG. 1 is a perspective view of the flexible tube portion of the endoscope of the present invention including the distal end and an intermediate section;

FIG. 2 is a perspective view similar to FIG. 1 wherein the endoscope has been made rigid and curved by operation of the control mechanism for the endoscope;

FIG. 3 is an enlarged cut-away perspective view of the distal end and flexible end segment of the endoscope shown in FIG. 1;

FIG. 4 is a cross sectional view of the flexible end segment of the endoscope shown in FIG. 3 taken along the line 4—4;

FIG. 5 is a cross sectional view along the longitudinal axis of the endoscope shown in FIG. 2 taken along the line 5—5.

FIG. 6 is a perspective view of a control mechanism for the endoscope of the invention;

FIG. 7 is a schematic, cross sectional view of a check valve associated with the control mechanism;

FIG. 8 is a cross sectional schematic view of the control mechanism of FIG. 6.

DESCRIPTION OF THE PREFERRED EMBODIMENT

Figure 9:
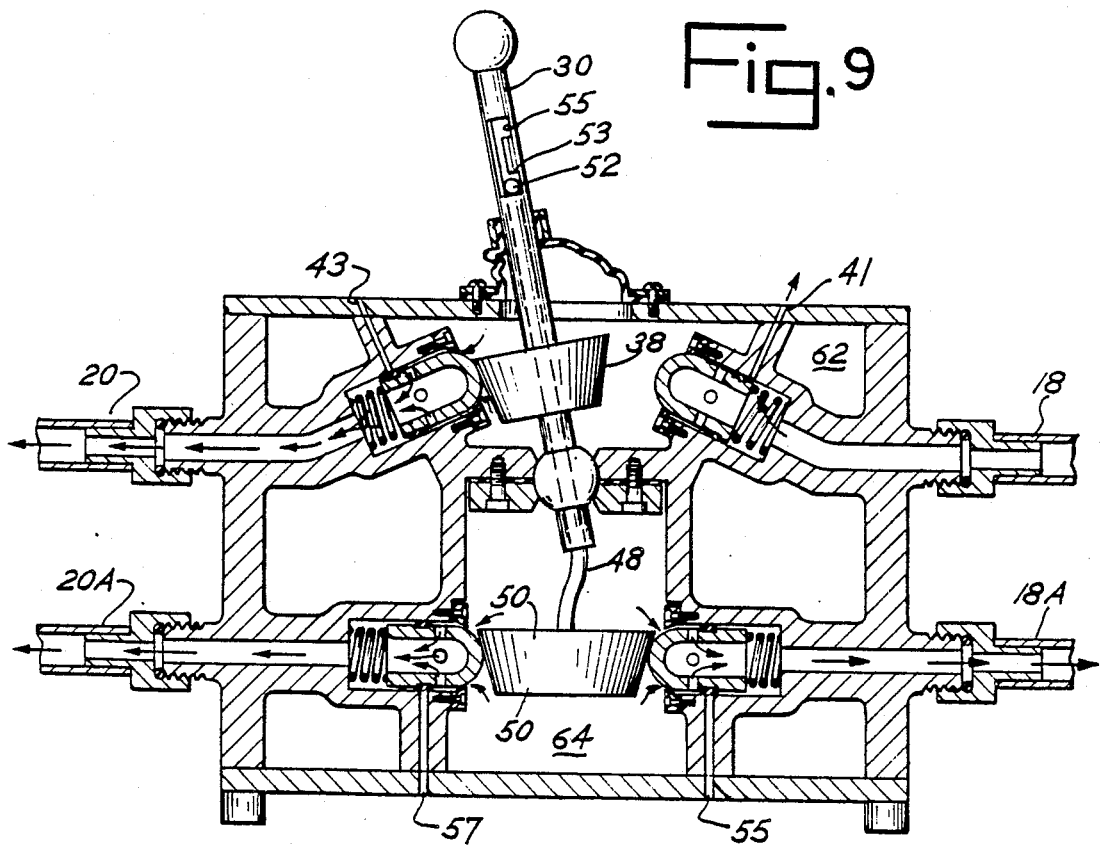
FIG. 9 is yet another cross sectional view of the control mechanism of FIG. 6 similar to FIG. 8.

FIG. 1 illustrates, in a perspective view, a flexible tube 10 near the distal end 12 of an endoscope device incorporating the invention. The tube 10 may be curved in a desired direction or made rigid when appropriate. The construction thus permits adjustment of rigidity as well as curvature. That is, if the tube is too flexible, then it cannot be easily guided into a body cavity. If it is too stiff, then it cannot comfortably be directed through curved body cavities or canals. Thus, the present invention seeks to provide an endoscope tube wherein the stiffness of the tube is adjustable, and the curvature is also adjustable in order to most efficiently guide the tube through curved cavities or canals.

In the drawings, therefore, the flexible tube 10 of the endoscope is depicted. The instrument or proximal end of the endoscope is not depicted but may be of any construction known to those of ordinary skill in the art depending upon the particular medical or diagnostic instrument involved. Typically, the endoscope tube 10 has a hollow elongate passage 22 including, for example, a fiber optic member which extends the length of the tube 10 to provide not only a light source path but also a transmission lens. The fiber optic element thus connects with appropriate instruments at the proximal end of the instrument, as shown in the prior art references previously identified, for the purpose of permitting a visual diagnosis. In some instances, medical instruments are inserted into the passage 22 of tube 10 to provide for the taking of a biopsy, for example, or for other surgical or diagnostic purposes.

The tube 10 is preferably elastic. The flexible tube 10 is comprised of a series of connected segments 14. Each segment 14 has approximately the same dimensions in length and diameter and constitutes a continuous portion of the tube 10, although the dimensions of each segment 14 need not be identical. Each segment 14 is independently controlled insofar as stiffness and curvature by separate control means in the manner to be described below.

FIG. 2 illustrates a benefit that results from having each of the segments 14 independently controlled to provide, for example, a controlled amount of stiffness as well as curvature. Thus, the ultimate end segment 14A may be curved upwardly. The next adjacent segment 14B may be rigid and straight, and the next segment 14C may be curved downwardly.

Referring to FIG. 3 and subsequent figures, the construction and operation of the individual segments 14 is described by reference to the end segment 14A near the distal end 12 of the endoscope. Segment 14A has a centerline axis 16. A plurality of four specially constructed conduits 18, 19, 20 and 21 extend parallel to the longitudinal axis 16 within segment 14A. Each conduit 18, 19, 20, 21 is positioned at an equal radial distance from the axis 16 and is equally spaced on a cylindrical locus from one of the other conduits 18, 19, 20, 21. The interior part of the segment 14A is, in the preferred embodiment, hollow defining the hollow tubular passage 22 for receipt of an instrument or a fiber optic package as previously described. The instrument package or fiber optic package or the like, which is retained within the passage 22, is plastic, i.e. it assumes the curvature of segment 14A.

Each of the conduits 18, 19, 20 and 21 has a similar construction. That is, each conduit 18, 19, 20, 21 is generally tubular and is comprised of an elastic material having an accordion configuration or cross section, as depicted in FIG. 5, when the segment 14 is in a relaxed condition. That is, the cross sectional configuration of the conduit 21 is such that folds 23, defining the conduit 21, are not extended or elongated when the conduit 21 is not elastically stressed or is relaxed.

Further, each of the conduits 18, 19, 20 and 21 is closed or sealed at its distal end, e.g. end 19B. The opposite end, e.g. end 19C, is connected to a pressure source, for example, a gas or liquid pressure source. Admission of pressurized gas to a first pressure level within the conduits 18, 19, 20 and 21 will tend to cause the conduits 18, 19, 20, 21 to become rigid. This, in turn, will make the segment 14A rigid inasmuch as it is reinforced by the four parallel, inflated conduits 18, 19, 20, 21. In order to make the segment 14A rigid. the pressure in each of the conduits 18, 19, 20 and 21 should be maintained equal. Further, in such instance the pressure in each of the conduits 18, 19, 20, 21 should preferably be at a level which will not cause the conduits 18, 19, 20, 21 to expand in the direction of the longitudinal axis 16.

In order to effect curvature of the segment 14A, differential pressures are provided to the conduits 18, 19, 20 and 21. For example, referring to FIG. 5, pressure in the conduit 19 is increased and pressure in the conduit 21 is maintained at an ambient pressure or decreased relative that in conduit 19 in order to cause curvature of the segment 14A. Thus, the conduit 19 is pressurized a sufficient amount to cause the conduit 19 to, in essence, elastically elongate or extend axially. Simultaneously the pressure in the conduit 21 may be maintained at an ambient level. Alternatively, a vacuum or a partial vacuum may be provided within the conduit 21. This will cause the segment 14A, which receives the conduit 21, to assume an arcuate or curved shape as depicted. Curvature of segment 14A results since the conduit 19 becomes elongated and the conduit 21 remains the same length or foreshortens.

To insure such curvature, the opposite ends of each conduit 18, 19, 20, 21 are preferably fixed to the segment 14A whereas the portion of the conduits 18–21 intermediate the ends is not fixed to the segment 14A, but rather rides in a passage in segment 14A. For example, conduit 19 is fixed to segment 14A at conduit ends 19B and 19C. Intermediate the ends 19B and 19C, the conduit 19 is slidable in a passage in segment 14A. The conduit 19, when initially inflated will thus become rigid and maintain a length equal to the original spacing of ends 19A and 19B. As the pressure in conduit 19 increases beyond a threshold elastic pressure limit, the conduit 19 elongates thereby elongating one side of the segment 14A. Segment 14A is thus somewhat elastic so as to respond to the elongation resulting when the conduit 19 is inflated and elongated.

Curvature in any direction can be effected by increasing the pressure in the manner described in any one or two of the four conduits, 18, 19, 20 or 21. By providing variable increased pressure to combinations of adjacent conduits, it is possible to effect highly controlled curvature of the segment 14A. Note that each of the conduits 18, 19, 20 and 21 is elastic. Thus, when pressure that causes elastic elongation of a conduit 18–21 is removed from the conduit 18, 19, 20 or 21, the conduit 18, 19, 20 or 21 will resume its original shape. The segment 14A thus, being slightly elastic, responds to the pressure pattern imparted by the elastic conduits 18, 19, 20 and 21.

In practice, four conduits 18, 19, 20, 21 provide sufficient means for control of curvature of each segment 14. However, additional conduits may be provided in a radially spaced pattern about the centerline axis 16 in order to further enhance the control of the endoscope segment 14. Further, in practice each endoscope segment 14 includes its own separate set of conduits which are elastic and expandable in the manner described. In this manner each segment 14 of the endoscope is separately controllable in terms of rigidity as well as curvature.

FIGS. 6, 7, 8 and 9 illustrate a type of pressure control device which may be used to control pressure in conduits 18–21 and thus the rigidity and curvature of the segment 14. As shown in FIGS. 6 and 7, the conduits 18, 19, 20 and 21 connect to a control box 28 having a control lever 30 pivotally mounted on a bearing 32 in a seat 34 in a throughbore in a plate 33 within the housing 28. Plate 33 separates the housing 28 into a high pressure chamber 62 and a low pressure chamber 64. Suitable, variable pressure sources 61, 63 are attached to chambers 62, 64, respectively.

The lever 30 includes a rigid, hollow cylindrical rod 36 which supports a valve actuator 38. The end of the rod 36 is connected with the bearing 32. In this manner the rod 36 is pivotal so as to permit the actuator 38 to engage either valve 40 or 42, for example, associated with conduits 18 and 20, respectively. The valves 40 and 42 are spring biased by associated springs 44 and 46 to the closed position until one of them is actuated by the actuator 38 due to pivoting of the rod 36. When in the closed position, valves 40, 42 are positioned to vent associated conduits 18, 20 to atmosphere via vent passages 41, 43.

The hollow rod 36 includes a telescopically received, flexible rod 48 supporting a second actuator 50. The rod 48 may be telescopically extended to the position shown in FIG. 9 by means of a lever 52 which can be positioned in a lower notch 53 rather than an upper notch 55 defined in hollow rod 36. Thus, the actuator 50 may be positioned for simultaneous engagement or disengagement with valves 54 and 56 which are normally closed due to actuation of associated springs 58 and 60. The valves 54 and 56 are associated respectively with the conduits 18A and 20A in FIG. 6. Conduits 18A, 20A are vented to atmosphere via vents 55, 57 when valves 54, 56 are closed.

The operation of the controls will be described with respect to the conduits 18 and 20. To control rigidity only, pressure from chamber 64 is provided via all conduits 18A, 20A (also 19A, 21A) simultaneously. Thus, the lever 52 is in the position illustrated in FIG. 9 in a lower notch 53 rather than an upper notch 55 of rod 36. The actuator 50 thus will simultaneously engage the ball valves 54, 56 thereby providing low pressure through conduits 18A, 20A through check valves 70 to the conduits 18, 20. When controlling rigidity in this manner, the lever 30 is maintained in a neutral or center rest position.

To control curvature, the control lever 30 may be actuated by movement in any direction to thereby effect high pressure flow to any of the conduits 18, 19, 20 or 21. Thus, in order to effect curvature associated with elastic pressurization of the conduits 18, the lever assembly 30 is pivoted in a counterclockwise sense as illustrated in FIG. 9 to open ball valve 42. This closes vent 43 and imparts high pressure from the chamber 62 through the valve 42 to the line 20. No simultaneous pressure is provided to the conduit 18. The high pressure in conduit 20 actuates check valve 70 in FIG. 7 to permit fluid flow to the conduit 20 in segment 14. This results since pressure in chamber 62 exceeds pressure in chamber 64 causing valve 70 to switch to the high pressure source. To effect the opposite curvature, the lever assembly 30 is pivoted in the clockwise direction. This actuates the ball valve 40 and closes vent 41. Valve 42 closes and vent 43 opens.

Conduits 19 and 21 are similarly controlled with respect to the use of ball valves and the like. In this manner it is possible to effect complete control of the rigidity and curvature of a segment of the endoscope tube 10. Such a lever assembly is typically provided for each segment 14 of the endoscope. In practice, only one or two lever assemblies need to be utilized inasmuch as only one or two segments 14 will be needed in order to guide an endoscope tube 10 appropriately into position. The pressure in the chamber 64 is also preferably variable in order to adjust the rigidity of the segments 14 as determined by the pressure within each of the separate conduits 18–21.

In sum, lever 30 controls curvature. Flexible rod 52 controls rigidity. Rigidity requires low pressure relative to the higher pressure curvature control.

It is possible to vary the construction of the invention in numerous ways. For example, each of the separate segments 14A, 14B and 14C may be connected to a separate control mechanism for purposes of controlling rigidity. Each of the separate control mechanisms can be adjustable to provide various levels of pressurization of that separate segment. With increased pressurization of a segment, there is increased rigidity.

It is also possible to interconnect the conduits 18–21 of separate segments 14A–14C by means of threshold check valves. Thus, the segments 14A–14C will be sequentially pressurized as increasing thresholds of pressure are reached.

Yet a further alternative construction would provide for use of a single control mechanism which could connect to any one of the separate segments 14A, 14B, 14C, etc. The connection to each of the separate segments 14A, 14B, 14C, etc. is controlled by a selector switch.

As a further feature of the invention, an elastic distal end segment may connect to one or more of the conduits 18–21. The distal end segment can then be inflated and function as a dilator to help advance movement of the endoscope into a body canal or cavity. Further, the invention can be constructed so that the conduits 18–21 are always equally pressurized to merely provide a means to render the segments 14 rigid. Also, separate means such as known to those of ordinary skill in the art can be used to control the curvature of the segments 14 or tube 10. For example, it is known to use various wire control systems which mechanically operate to curve the tube 10. Such a mechanical system can be used in combination with the conduit system of the present invention.

Yet another option is to provide alternate means for venting the conduits 18–21 whenever the associated valve connecting that conduit to a pressure source is released. It is also possible to vary the construction of the conduits. That is, an accordion-type cross section has been disclosed. However, the cross sectional shape, size and configuration of the conduits, for example conduit 18, may be varied in accord with desires to achieve various types of control upon inflation as well as upon the elastic deformation.

Further, the number of conduits used in each segment may be varied. The number of control segments can be varied. The particular arrangement of the conduits relative to the center line axis of the tube can be varied. The choice of materials can be varied. The interconnection or interrelationship of the conduits 18–21 to the tube 10 can be varied. The conduits may be, for example, integrally molded or formed in the tube 10. Alternatively, the conduits may be made of a separate material having distinct elastic and plastic characteristics relative to the material used to form the tube 10. Though a toggle stick or joy stick mechanism for controlling pressure to each of the separate conduits is disclosed, numerous other types of control mechanisms are possible to vary the pressure to each of the separate conduits in each of the separate segments.

Thus, while there has been set forth a preferred embodiment of the invention, it is to be understood that the invention is to be limited only by the following claims and their equivalents.

What is claimed is:

1. In a flexible endoscope of the type including an elongate flexible tube having a distal end and a proximal end; and
   a medical procedure system having at least a part thereof extending through the tube from the proximal end to the distal end, said system being capable of transmitting diagnostic data from the distal end to the proximal end or conducting a medical procedure at the distal end from the proximal end;
   the improvement comprising, in combination:
   means within the tube for controlling the curvature of a longitudinal segment of the tube; and
   means external the tube for controlling the means within the tube segment;
   said means for controlling curvature comprising at least one flexible tube segment, said segment having a longitudinal center axis, said segment further including at least two longitudinal, flexible, hollow conduits generally parallel to the axis, said conduits each being elastically deformable in the longitudinal direction in response to increased pressure within the conduits; and
   said means for controlling comprising means for inflating the conduits independently by increasing fluid pressure in one of the conduits beyond the plastic limit to thereby elastically deform the conduit in the longitudinal direction and effect elongation of said conduit and attached tube to thereby effect controlled curvature of the tube segment.

2. The endoscope of claim 1 including a plurality of conduits equally spaced in a radial direction from the axis.

3. The endoscope of claim 1 including a plurality of at least four conduits equally radially spaced from the axis and equally spaced from one another.

4. In a flexible endoscope of the type including an elongate flexible tube having a distal end and a proximal end; and
   a medical procedure system having at least a part thereof extending through the tube from the proximal end to the distal end, said system being capable of transmitting diagnostic data from the distal end to the proximal end or conducting a medical procedure at the distal end from the proximal end;
   the improvement comprising, in combination:
   means within the tube for controlling the curvature of a longitudinal segment of the tube; and
   means external the tube for controlling the means within the tube segment;
   said means for controlling curvature comprising at least one flexible tube segment, said segment having a longitudinal center axis, said segment further including at least two longitudinal, flexible, hollow conduits generally parallel to the axis, said conduits each being elastically extensible in the longitudinal direction in response to increased pressure within the conduit; and
   said means for controlling comprising means for inflating the conduits independently by increasing fluid pressure in one of the conduits beyond the plastic limit to thereby elastically extend the conduit in the longitudinal direction and effect elongation of said conduit and attached tube to thereby effect controlled curvature of the tube segment.

5. The endoscope of claim 4 including a plurality of conduits equally spaced in a radial direction from the axis.

6. The endoscope of claim 4 including a plurality of at least four conduits equally radially spaced from the axis and equally spaced from one another.

* * * * *